United States Patent [19]

Matsumoto et al.

[11] Patent Number: 4,824,876
[45] Date of Patent: Apr. 25, 1989

[54] LIGHT CURABLE DENTAL LIQUID OR PASTE

[75] Inventors: Takeo Matsumoto; Eiichi Yamada, both of Ibaraki; Osamu Nakachi, Yokohama; Godo Irukayama; Yoshihiro Minoshima, both of Ibaraki, all of Japan

[73] Assignee: Nippon Oil and Fats Co., Ltd., Tokyo, Japan

[21] Appl. No.: 29,287

[22] Filed: Mar. 23, 1987

Related U.S. Application Data

[63] Continuation-in-part of Ser. No. 768,546, Aug. 23, 1985, Pat. No. 4,746,685.

[30] Foreign Application Priority Data

Aug. 31, 1984 [JP] Japan .................. 59-180268
Dec. 29, 1984 [JP] Japan .................. 59-275895
Feb. 26, 1985 [JP] Japan .................. 60-35342

[51] Int. Cl.$^4$ .................. C08F 2/50; C08F 4/36; C08F 265/06
[52] U.S. Cl. .................. 522/24; 522/13; 522/102; 522/120; 522/908; 522/116; 525/303
[58] Field of Search .................. 522/24, 13

[56] References Cited

U.S. PATENT DOCUMENTS

| | | | |
|---|---|---|---|
| 4,416,826 | 11/1983 | Neckers | 522/33 |
| 4,459,193 | 7/1984 | Ratcliffe | 522/24 |
| 4,474,868 | 10/1984 | Yamaoka | 522/24 |
| 4,525,232 | 6/1985 | Rooney | 522/24 |
| 4,533,446 | 8/1985 | Conway | 522/24 |
| 4,674,980 | 6/1987 | Ibsen | 522/24 |
| 4,777,191 | 10/1988 | Komai | 522/46 |

FOREIGN PATENT DOCUMENTS 197401 11/1984 Japan .

OTHER PUBLICATIONS

Chimia Y Technologia, vol. 6, 1980, pp. 23-25.
Komai, J59-197401 of Nov. 9, 1984, Japio Abstract No. 84-197401.
Komai, EP-126541 of Nov. 28, 1984, Derwent Abstract No. 84-295941/48.

Primary Examiner—John C. Bleutge
Assistant Examiner—A. H. Koeckert
Attorney, Agent, or Firm—Jordan and Hamburg

[57] ABSTRACT

A light curable dental liquid or paste comprises an ethylenic unsaturated monomer, a light polymerization initiator and an organic filler. The light polymerization initiator is a combination of an organic peroxide and a pyrylium salt compound of:

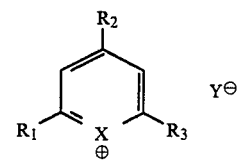

wherein $R_1$, $R_2$ and $R_3$ each represents a hydrogen atom, an alkyl group and the like, X stands for an oxygen or sulfur atom and Y for an anionic functional group.

14 Claims, No Drawings

LIGHT CURABLE DENTAL LIQUID OR PASTE

CROSS-REFERENCE TO RELATED APPLICATION

This application is a continuation-in-part application of application Ser. No. 768,546 filed Aug. 23, 1985, now U.S. Pat. No. 4,764,685.

BACKGROUND OF THE INVENTION

1. Field of the Invention

The present invention relates generally to a light curable dental liquid or paste, and more particularly to a dental liquid or paste which can be cured by irradiation of light to be utilized for teeth crown materials, denture base materials, dental cementing materials, dental bonding materials, dental filling materials, dental impression materials and caries-preventive materials.

2. Related Art Statement

Heat-polymerizable dental compositions wherein organic peroxides, such as benzoyl peroxide, are used as the polymerization initiators and cold-setting type dental compositions wherein Redox type polymerization initiators, such as a combination of benzoyl peroxide with a tertiary amine, are used as the polymerization initiators have been known in the art. Further known in the art is a composition containing a sensitizer such as benzoin alkyl ether to be cured by irradiation of ultraviolet rays.

However, the known heat-polymerizable and cold-setting type dental compositions have a disadvantage that the cured resins tend to contain air bubbles which lower the mechanical strength and water-proof properties, since they are prepared by mixing a powder with a liquid or kneading a paste with another paste. In addition, the heat-polymerizable dental compositions have another disadvantage that a complicated and time-consuming operation is required for polymerization. On the other hand, the cold-setting type dental compositions have additional disadvantages that the curing speed thereof is too high, which causes difficulties in clinical operation, and that the formed denture is colored, which deteriorates the appearance thereof, due to the undesirable action by the tertiary amine.

Compositions containing an ordinary light polymerization initiator sensitive to ultraviolet rays, such as benzoin alkyl ether, give rise to problems that the transmittance to ultraviolet rays effective for polymerization or curing is so low as to limit the depth of cured composition only to less than 2 mm, resulting in unsatisfactory curing depth, that a filter or other protection means is indispensable since the ultraviolet rays contain the rays having wavelengths of less than 320 nm which are harmful to human beings, and that the lifetime of a mercury lamp used as the irradiation source is short.

Further known in the art is a one-paste type dental composition containing a light polymerization initiator. However, the known dental composition of this type has disadvantages that the mechanical strength, particularly the bending strength, of the cured product is low, and that it is inferior in ease of handling or operation when used in practical operation.

OBJECTS AND SUMMARY OF THE INVENTION

A primary object of this invention is to provide a light curable dental liquid or paste which can be readily cured by irradiation of light within a short time period to give a product which is set deep into the interior region thereof.

Another object of this invention is to provide a light curable dental liquid or paste which is inexpensive and excellent in curing property, and yet ensures safe and easy operation in clinical application.

A further object of this invention is to provide a light curable dental liquid or paste which has a surface of lower adhesiveness to make the handling in clinical operation easier and forms a cured product having higher mechanical strength including bending strength and having low percent shrinkage.

The above and other objects of the invention will become apparent from the following description.

According to the present invention, there is provided a light curable dental liquid or paste comprising an ethylenic unsaturated monomer, a light polymerization initiator and an organic filler, said light polymerization initiator comprising a combination of an organic peroxide and a pyrylium salt compound represented by the following general formula [I] of:

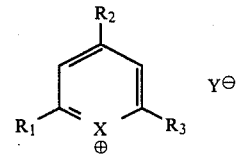

wherein $R_1$, $R_2$ and $R_3$ each represents the same or different atom or group and stands for a hydrogen atom, a halogen atom, an alky group, a haloalkyl group, an ethylenyl group, a styryl group, an alkoxy group, a phenyl group, a naphthyl group, an alkylphenyl group, an alkylstyryl group, an alkylnaphthyl group, an alkoxyphenyl group, an alkoxystyryl group, an alkoxynaphthyl group, a hydroxyphenyl group, a hydroxystyryl group, a hydroxynaphthyl group, a halophenyl group, a halostyryl group, a halonaphthyl group, a nitrophenyl group, a nitrostyryl group, a nitronaphthyl group, an aminophenyl group, an aminostyryl group, an aminonaphthyl group, an alkylaminophenyl group, an alkylaminostyryl group, an alkylaminonaphthyl group, a nitro group, an amino group or a hydroxyl group, X stands for an oxygen atom or a sulfur atom and Y for an anionic functional group.

DESCRIPTION OF THE INVENTION

The present invention will be described in detail hereinbelow.

The light curable dental liquid or paste, according to the invention, comprises an ethylenic unsaturated monomer and one or more of specific light polymerization initiators.

Any ethylenic unsaturated monomers which have been conventionally used in dental compositions may be used conveniently in the composition of the invention, examples being derivatives of methacrylic acid, such as methyl methacrylate, 2-hydroxyethyl methacrylate, neopentylglycol dimethacrylate, 1,4-butanediol dimethacrylate, ethyleneglycol dimethacrylate, diethyleneglycol dimethacrylate, triethyleneglycol dimethacrylate, polyethyleneglycol dimethacrylate, propyleneglycol dimethacrylate, dipropyleneglycol dimethacrylate, tripropyleneglycol dimethacrylate, polypropyleneglycol dimethacrylate, tetromethylolmethane trimethacrylate, tetramethylolmethane tetramethacrylate, hexamethyleneglycol dimethacrylate, 2,2-bis(4-methacryloxyphenyl)propane, 2,2-bis(4-methacryloxyethoxyphenyl)propane, 2,2-bis(4-methacryloxypolyethoxyphenyl)propane, 2,2-bis[4-(3-methacryloxy-2-hydroxypropoxy)phenyl]propane, 1,2-bis(3-methacryloxy-2-hydroxypropoxy)ethane, 2,2-bis(4-methacryloxyphenyl)propane, 2-hydroxy-1,3-dimethacryloxypropane, di-2-methacryloxyethyl-2,2,4-trimethylhexamethylene dicarbamate, 2-hydroxy-3-phenoxypropyl methacrylate, 2-hydroxy-3-p-t-butylphenoxypropyl methacrylate, methacryloxyethylphenylphosphoric acid, 4-methacryloxyethyl trimellitate anhydride and mixtures thereof. Other derivatives of acrylic acid, styrene and derivatives of styrene may also be used in the present invention. Curable resin having maleate, fumarate, allyl or (meth)acrylate groups, unsaturated polyester resins, unsaturated acrylic resins, or acrylate oligomers modified with isocyanate, polyester-acryl oligomers, polyether-acryl oligomers, etc. may be used in the present invention.

The specific light polymerization initiator which may be used in the invention is a combination of an organic peroxide and a pyrylium salt compound represented by the following general formula [I] of:

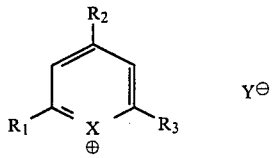

wherein $R_1$, $R_2$ and $R_3$ each represents the same or different atom or group and stands for a hydrogen atom, a halogen atom, an alkyl group, a haloalkyl group, an ethylenyl group, a styryl group, an alkoxy group, a phenyl group, a naphthyl group, an alkylphenyl group, an alkylstyryl group, an alkylnaphthyl group, an alkoxyphenyl group, an alkoxystyryl group, an alkoxynaphthyl group, a hydroxyphenyl group, a hydroxystyryl group, a hydroxynaphthyl group, a halophenyl group, a halostyryl group, a halonaphthyl group, a nitrophenyl group, a nitrostyryl group, a nitronaphthyl group, an aminophenyl group, an aminostyryl group, an aminonaphthyl group, an alkylaminophenyl group, an alkylaminostyryl group, an alkylaminonaphthyl group, a nitro group, an amino group or a hydroxyl group, X stands for an oxygen atom or a sulfur atom and Y for an anionic functional group.

A single or a combination of two or more organic peroxides, each having one or more oxygen-oxygen bonds in one molecule, may be used in the invention. The organic peroxides include a polyperoxy ester containing a benzophenone group and represented by the following general formula [II] of:

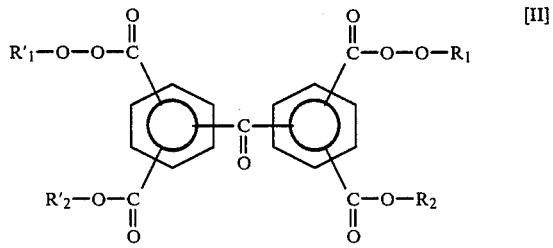

wherein $R_1$ and $R_1'$ each represents the same or different group and stands for a tertiary alkyl group having 4 to 8 carbon atoms or a tertiary aralkyl group having 9 to 12 carbon atoms and $R_2$ and $R_2'$ each represents the same or different atom or group and stands for a hydrogen atom, a tertiary alkoxy group having 4 to 8 carbon atoms or a tertiary aralkyloxy group having 9 to 12 carbon atoms. The specific examples of the organic peroxides which may be used in the invention include methyl ethyl ketone peroxide, cyclohexanone peroxide, acetylacetone peroxide, 1,1-bis(t-butylperoxy)cyclohexane, t-butylhydroperoxide, cumene hydroperoxide, diisopropylbenzene hydroperoxide, p-menthane hydroperoxide, di-t-butyl peroxide, t-butylcumyl peroxide, dicumyl peroxide, 2,5-dimethyl-2,5-di(t-butylperoxy)hexane, acetyl peroxide, octanoyl peroxide, lauroyl peroxide, 3,5,5-trimethylhexanoyl peroxide, benzoyl peroxide, diisopropylperoxy dicarbonate, di-2-ethylhexylperoxy dicarbonate, di(3-methyl-3-methoxybutyl)peroxy dicarbonate, t-butylperoxy isobutylate, t-butylperoxy octanoate, t-butylperoxy benzoate, di-t-butyldiperoxy isophthalate, 2,5-dimethyl-2,5-di(benzoylperoxy)hexane, 3,3',4,4'-tetra(tertiary-butylperoxycarbonyl)benzophenone, tri(t-butylperoxy)trimellitate, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-isopropylcumylperoxycarbonyl)benzophenone, and mixtures thereof.

A single or a combination of two or more pyrylium salt compounds may be used in the invention, and the examples of the pyrylium compound include pyrylium salts and thiopyrylium salts represented by the general formula [I] wherein the anionic functional group Y is perchlorate, fluoroborate, fluorophosphonate, fluoroantimonate, chloroaluminate, sulphuracetate, methosulfate, thiocyanate, sulfate, nitrate or acetate.

The specific examples of the compounds represented by the general formula [I] will be listed as follows: 4-(4-butoxyphenyl)-2,6-bis(4-methoxyphenyl)pyrylium fluoroborate, 4-(4-butoxyphenyl)-2,6-diphenylthiopyrylium fluoroborate, 4-(4-butoxyphenyl)-2,6-bis(4-methoxyphenyl)thiopyrylium fluoroborate, 2,6-bis(4-methoxyphenyl)-4-phenylthiopyrylium fluoroborate, 4-(4-butoxyphenyl)-2,6-diphenylpyrylium fluoroantimonate, 2-methyl-4,6-bis(4-methoxyphenyl)thiopyrylium fluoroborate, 2,4,6-tri(4-methoxyphenyl)thiopyrylium perchlorate, 2,4,6-tri(4-methoxyphenyl)thiopyrylium fluoroborate, 4-(3,4-diethoxyphenyl)-2,6-bis(4-methoxyphenyl)thiopyrylium fluoroborate, 4-(4-dimethylaminophenyl)-2,6-diphenylthiopyrylium perchlorate, 2-nitro-4,6-bis(4-dimethylaminostyryl)pyrylium fluoroborate, 2-methoxy-4-naphthyl-6-styrylthiopyrylium fluoroborate, 2-amino-4,6-bis(4-butoxyphenyl)thiopyrylium perchlorate, 2-(4-nitrophenyl)-4,6-bis(4-butylphenyl)thiopyrylium fluoroborate, 2-hydroxy-4,6-bis(4-dimethylaminostyryl)pyrylium perchlorate, 2-(3,4-dichlorophenyl)-4-(4-methoxyphenyl)-6-phenylpyrylium fluoroborate and mixture thereof.

The pyrylium or thiopyrylium salt which acts as a sensitizer is contained in the composition preferably in an amount of 0.001 to 1 part by weight, more preferably 0.001 to 0.5 part by weight, based on 100 parts by weight of the ethylenic unsaturated monomer. If the content of the sensitizer is less than 0.0001 part by weight, the dental liquid or paste can not be cured by irradiation with visible rays, whereas the content of the sensitizer in excess of 1 part by weight is undesirable for the reason that the thickness of cured layer (i.e. the depth of curing) is conversely decreased and for hygienic reason.

Preferable content of the organic peroxide ranges within 0.001 to 10 parts by weight, more preferably within 0.01 to 5 parts by weight, based on 100 parts by weight of the ethylenic unsaturated monomer. If the content of the organic peroxide is less than 0.001 part by weight, the composition is not curable, whereas the content thereof in excess of 10 parts by weight is undesirable because of the deterioration of the properties of the cured product.

When a combination of the organic peroxide and the sensitizer is used as the light polymerization initiator, the composition may be readily cured by irradiation with visible rays having a wavelength of from 400 nm to 700 nm for a short time so that the depth of curing reaches not less than 5 mm to make the composition well adapted for dental uses.

The light curable dental liquid or paste according to the invention contains an organic filler. The organic filler may preferably be a polymer obtained by polymerizing a feed monomer containing at least an ester of carboxylic acid such as (meth)acrylate. It is desired that the polymer be a linear polymer containing not less than 80% by weight, more preferably not less than 90% by weight, of the (meth)acrylate units and having a weight average molecular weight of not more than 500,000, preferably not more than 200,000. If the linear polymer contains not less than 80% by weight of (meth)acrylate units, excellent solubility and viscosity for use as the dental liquid or paste are attained. If the weight average molecular weight exceeds 500,000, viscosity tends to increase, thus resulting in difficulties in handling when clinically used.

The specific examples of the ester of carboxylic acid which may be used as the feed monomer include methyl(meth)acrylate, ethyl(meth)acrylate, propyl(meth)acrylate and butyl(meth)acrylate.

The feed monomer to be polymerized to form a polymer usable as the organic filler may contain an unsaturated comonomer copolymerizable with the ester of carboxylic acid. The preferred unsaturated comonomer is represented by the following general formula [III] of:

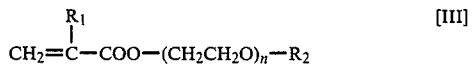

$$CH_2=C-COO-(CH_2CH_2O)_n-R_2 \quad [III]$$
$$\phantom{CH_2=C}|\phantom{-COO-(CH_2CH_2O)_n-R_2}$$
$$\phantom{CH_2=}R_1$$

wherein $R_1$ is a hydrogen atom or a methyl group, $R_2$ is an alkyl group having 1 to 4 carbon atoms or a phenyl group, and n is an integer of 1 to 15. The copolymers prepared from unsaturated comonomers represented by the general formula [III] wherein n exceeds 15 are not preferred, since they become so hydrophilic as to have lower water-proof property of the product composition.

The specific examples of the unsaturated comonomer represented by the general formula [III] include methoxyethyl(meth)acrylate, phenoxyethyl(meth)acrylate, methoxydiethyleneglycol(meth)acrylate, methoxytetraethyleneglycol(meth)acrylate, isobutoxytetraethyleneglycol(meth)acrylate, methoxypolyethyleneglycol(meth)acrylate, ethoxypolyethyleneglycol(meth)acrylate, isopropoxypolyethyleneglycol(meth)acrylate, isobutoxypolyethyleneglycol(meth)acrylate, phenoxypolyethyleneglycol(meth)acrylate and mixtures thereof. In the specific examples listed above, "poly" means that n indicating the number of respective repeating units ranges within 5 to 15.

The aforementioned copolymers may be prepared through ordinary solution polymerization, suspension polymerization or emulsion polymerization while using a radical polymerization initiator. The molecular weight of the copolymer ranges preferably from 10 to 500 thousands in consideration of solubility and lower adhesiveness.

The organic filler may be added in any form including fine particles, fibers, beads, whiskers or microplates. It is preferred that 0.1 to 90 parts by weight, more preferably, 0.1 to 80 parts by weight of the organic filler be added to 10 to 99.9 parts by weight of the ethylenic unsaturated monomer. The dental liquid or paste containing the components in the above defined range has a suitable viscosity and a low surface tackiness for easy application in clinical operation, and is cured to form a cured mass having excellent mechanical strength, particularly superior bending strength and low percent shrinkage.

The light curable dental liquid or paste, according to the invention, may contain fine particles of inorganic filler. Preferable inorganic filler used for this purpose include apatite, soda-lime glass, silica, quartz, borosilicate glass, alumina, barium oxide, zirconium glass and mixtures thereof. A particularly preferred inorganic filler is a silica having an average particle size of from 1 to 100 millimicrons and being treated to be hydrophobic with a treating agent, such as dimethyldichlorosilane, hexamethyldisilazane, octyltrimethoxysilane or silicone oils, because such silica is improved in light transmittance, water-proof property and thixotropy.

It is desirous that 10 to 99.9 parts by weight of one or more of the ethylenic unsaturated monomer are mixed with 50 to 5 parts by weight of fine particles of one or more of the aforementioned inorganic fillers and 0.1 to 90 parts by weight of one or more of the aforementioned organic filler.

The dental liquid or paste of the invention may further contain an additional dental filling material which has been ordinarily used in dental application. Examples of such a dental filling material are apatite, soda-lime glass, silica, quartz, silica gel, borosilicate glass, synthetic sapphire (alumina) and radioactive opaque filling materials, such as barium oxide and zirconium glass. The dental filling material may be in the form of beads, micro-powders, micro-plates, fibers or whiskers, or may have irregular shapes. In addition to the aforementioned ingredients, as appropriate amount of other dental additives, such as binder resin, polymerization inhibitor, antioxidant, stabilizer, pigment, dye or viscosity increasing agent, may be added, as desired.

The dental liquid or paste of the invention may be mixed by a manufacturer, charged into a sealed container in the form of a composite liquid or paste, and supplied to a dentist or a dental technician. A dentist or dental technician may apply or fill the dental composition of the invention thus supplied to mold the same, and then the composition is irradiated by a light from an irradiation source to be polymerized and cured.

Any irradiation sources may be used for curing the composition of the invention as far as they generate light havihng wavelengths within the aforementioned range, examples including a xenon lamp, a halogen lamp, a tungsten lamp, a fluorescent lamp, a metal halide lamp and a laser.

The dental liquid or paste of the invention can be cured readily by irradiation of light within a short time period to be cured deeper in the interior region and is superior over the conventional composition using a polymerization initiator sensitive to ultraviolet rays. The dental liquid or paste of the invention is further improved in safe and easy handling in clinical operation and from an economical viewpoint.

EXAMPLES OF THE INVENTION

The present invention will now be described more specifically by referring to examples and comparative examples. It should be noted that the following examples are given by way of illustration only and the present invention is not limited to these specific examples. It is also to be understood that, in the following, the parts or percentages shall denote those by weight.

EXAMPLES 1 AND 2 AND COMPARATIVE EXAMPLE 1

Preparation of Organic Filler

A polymer was prepared by the conventional solution polymerization process from a starting composition of 50 parts of methoxydiethyleneglycol monomethacrylate, 40 parts of methyl methacrylate and 10 parts of methoxytetraethyleneglycol monomethacrylate, using 2,2-azobisisobutyronitrile as the polymerization initiator and also using benzene as the solvent. The polymer was precipitated using petroleum ether to produce a solid organic filler (A)-1. The weight average molecular weight of the organic filler (A)-1 reached 150,000, as measured by the GPC method.

Polymer particles were produced by the conventional suspension polymerization process from a starting composition of 95 parts of methyl methacrylate, 3 parts of butyl methacrylate and 2 parts of diethyleneglycol dimethacrylate, using polyvinyl alcohol, calcium carbonate and sodium dodecylbenzenesulfonate as the dispersing agent and also using benzoyl peroxide as the polymerization initiator. These polymer particles were fractionated by precipitation dispersion and particles not larger than 50 microns in diameter were collected so as to be used as the organic filler (A)-2. Similarly, an organic filler (A)-3 with particle size of not larger than 20 microns was produced from a composition of 95 parts of methyl methacrylate, 3 parts of butyl methacrylate and 2 parts of diethyleneglycol dimethacrylate.

PREPARATION OF DENTAL PASTE

The light polymerization initiator and the organic filler (A)-1 specified in Table 1 were dissolved in an ethylenic unsaturated monomer at the composition ratio shown in Table 1. The solution was charged into a kneader, into which the inorganic filler and the organic filler (A)-2 or (A)-3 were gradually added and the resulting mixture was kneaded at an atmospheric pressure for two hours. The resulting product was further kneaded for two hours to produce a paste, while the pressure was reduced to not higher than 20 mmHg for de-foaming.

TEST

The pastes each having a composition ratio shown in Table 1 were irradiated with light for a prescribed time interval, using a light irradiator having four halogen lamps (150 W) to produce a cured product. Then, using the following methods, the impact strength, bending strength and the percent shrinkage of the cured product were measured.

Tackiness on the paste surface was evaluated by the finger touch method.

IMPACT STRENGTH

A cellophane sheet was laid in a prescribed stainless steel mold and the paste was injected under pressure on the sheet. Another cellophane sheet was placed on the upper surface of the paste and pressed from the upper side by a slide glass to obtain a uniform flat paste surface. With the slide glass removed, the light was irradiated from above for ten minutes for sufficient curing. Each of the cured products was taken out of the mold and shaped to a flat plate of 1.5 mm in length, 10 mm in width and 3 mm in thickness so as to be used as a test piece. After 24 hours after the termination of light polymerization, the cured product was subjected to an impact test. The test was conducted using an impact tester and the mean value derived from the test on five test pieces was adopted as the impact strength. The resultes are shown in Table 2.

BENDING STRENGTH

A cellophane sheet was laid over a stainless steel mold, and a paste was charged and pressed on the cellophane sheet. The top face of the paste was covered by another cellophane sheet, and then a slide glass plate was put thereon under a pressure to flatten the surface so that the molded paste had even side faces. Thereafter, the slide glass plate was removed, and the paste was exposed to irradiation of light from the top face thereof for 2 minutes to be cured sufficiently. The cured product or resin was taken out of the mold, and machined to form a test piece having a length of 60 mm, a width of 10 mm and a thickness of 2.5 mm. The test piece was aged for 24 hours after the light polymerization, and then subjected to bending test. The span between the fulcra carrying the test piece was set to 50 mm, and the bending strength of the test piece was measured at a cross-head speed of 2 mm/min using a bending tester attached to an autograph. The bending strength was calculated from the following equation of:

$$\text{Bending Strength [kg/cm}^2\text{]} = \frac{3Fl}{2bd^2} \text{ ;}$$

wherein F is the maximum stress applied to the test piece, I is the distance between the fulcra, b is the width of the test piece, and d is the thickness of the test piece.

Bending strengths of five test pieces for each cured resin were measured and the average value thereof was calculated. The results are shown in Table 2.

PERCENT SHRINKAGE

The density of the paste and that of the cured product obtained by the same procedure as that described above in connection with the impact strength were measured by the substitution-in-water method, using pure water of 23° C., and the percent shrinkage was obtained from the following formula:

$$\alpha = \left(1 - \frac{\rho_M}{\rho_P}\right) \times 100 \, (\%)$$

wherein $\rho_M$ denotes the density of the paste and $\rho_P$ denotes that of the cured product.

COMPARATIVE EXAMPLE 1

Tests similar to those in the above Examples were conducted on the composition shown in the Table 1. The results are shown in the Table 2.

TABLE 1

| Example | Ethylenic unsaturated monomer Note 1 | (wt. part) | Organic filler (wt. part) | | Inorganic filler Note 2 | (wt. part) | Initiator Note 3 | (wt. part) |
| --- | --- | --- | --- | --- | --- | --- | --- | --- |
| 1 | 3G | (25) | (A)-1 | (2) | S-1 | (25) | BTTB | (0.5) |
|  | MPEPP | (25) | (A)-2 | (25) |  |  | MBM | (0.005) |
| 2 | 3G | (30) | (A)-1 | (3) | S-1 | (25) | MBM | (0.05) |
|  | MPEPP | (30) | (A)-3 | (15) |  |  | TBT | (0.5) |
| Com. Ex. 1 | 3G | (35) | — |  | S-1 | (30) | BTTB | (0.5) |
|  | MPEPP | (35) |  |  |  |  | MBM | (0.005) |

Note 1:
3G: Triethyleneglycol dimethacrylate
MPEPP: 2,2-Bis(4-methacryloxypolyethoxyphenyl)propane
Note 2:
S-1: Silica treated with dimethyldichlorosilane having an average particle size of 20 mµ
Note 3:
BTTB: 3,3',4,4'-Tetra(t-butylperoxycarbonyl) benzophenone
MBM: 4-(4-Butoxyphenyl)-2,6-bis(4-methoxyphenyl)thiopyrylium fluoroborate

TABLE 2

| Example | Impact strength (Kgf/cm) | Bending strength (Kgf/cm$^2$) | Percent shrinkage (%) | Tackiness |
| --- | --- | --- | --- | --- |
| 1 | 2.1 | 840 | 3.0 | No |
| 2 | 2.5 | 850 | 4.0 | No |
| Com. Ex. 1 | 1.1 | 550 | 8.0 | Yes |

It is seen from the Examples 1 and 2 and the Comparative Example 1 that the percent shrinkage is effectively lowered by the contents of the organic filler particles (A)-1 and (A)-2 or (A)-3 in the composition while it is apparent from evaluation that the composition of the present invention is also superior in mechanical strength and clinical operability.

EXAMPLES 3 TO 5 AND COMPARATIVE EXAMPLE 2

Preparation of Organic Filler

A polymer was produced by the conventional solution polymerization process from the starting composition of 96 parts of methyl methacrylate, 3 parts of butyl methacrylate and 1 part of methacrylic acid, using 2,2-azobisisobutyronitrile as the polymerization initiator and also using benzene as the solvent. The polymer was precipitated, using petroleum ether to produce a solid organic filler (B)-1. The weight average molecular weight of the filler (B)-1 reached 150,000, as measured by the GPC method.

Similarly, an organic filler (B)-2 having a composition of 90 parts of methyl methacrylate, 5 parts of isopropyl methacrylate, 4 parts of butyl methacrylate and 1 part of 2-hydroxyethyl methacrylate was obtained. The weight average molecular weight of the filler amounted to 120,000.

PREPARATION OF DENTAL PASTE 0.5 part of 3,3',4,4'-tetra(t-butylperoxycarbonyl)benzophenone and 0.05 part of 4-(4-butoxyphenyl)-2,6-diphenylthiopyrylium fluoroborate were dissolved in 25 parts of triethyleneglycol dimethacrylate and 25 parts of 2,2-bis[4-(3-methacryloxy-2-hydroxypropoxy)phenyl]propane to produce a homogeneous solution, which was then charged into a kneader. Then, 30 parts of polymethylmethacrylate beads (BR-85, manufactured by Mitsubishi Rayon Co., Ltd.) were added into the kneader to form a slurry mixture, into which 20 parts of silica particles ("Aerosil R-972" manufactured by Nihon Aerosil Co., Ltd.) were added gradually and the resulting product was kneaded for two hours at an atmospheric pressure. The thus kneaded product was further kneaded for one hour while the pressure was reduced to 20 mmHg to produce a dental paste.

TEST

Each of the ethylenic unsaturated monomers, the organic fillers, the light polymerization initiators and the solvents having the composition ratios as shown in Table 3 was dissolved homogeneously to produce a light curable dental paste. The test on the adhesive properties thereof was conducted by the following method.

Using acrylic resin for denture base ("Acron" produced by G-C Dental Industrial Corp.), a column of 15 mm in diameter and 10 mm in height was prepared. On this column was bonded a silicone frame of 2 mm in thickness and having an aperture of 5 mm in diameter, using a double-sided adhesive tape. The dental paste was filled in the aperture and the light was radiated from above for 10 minutes from a 150 W halogen lamp for polymerization and curing. The resulting cured product was allowed to stand at 38° C. for 24 hours so as to be used as a test piece. The load was applied to the superposed adhesion zone from the lateral side at a crosshead speed of 2 mm per minute, using an adhesion tester comprised of the test piece and an autograph attached thereto. The results are shown in Table 3.

COMPARATIVE EXAMPLE 2

Similar tests as in the Examples were conducted on the dental composition shown in Table 3. The results are also shown in Table 3.

TABLE 3

| Example | Ethylenic unsaturated monomer Note 1 | (wt. part) | Organic filler (wt. part) | Initiator Note 2 | (wt. part) | Solvent (wt. part) | Adhesive strength (Kgf/cm²) |
|---|---|---|---|---|---|---|---|
| 3 | MMA | (65) | (B)-2 (20) | BPT | (0.08) | Ethyl | 210 |
|   | 2G | (9) |   | TBT | (0.8) | acetate (6) |   |
| 4 | MMA | (80) | (B)-1 (10) | BPT | (0.08) | Methylene | 220 |
|   | BD | (9) |   | BTTB | (0.8) | chloride (1) |   |
| 5 | MMA | (70) | (B)-1 (10) | BPT | (0.08) | Ethyl | 230 |
|   |   |   |   |   |   | acetate (0.5) |   |
|   | 1G | (9) | (B)-2 (10) | BTTB | (1.6) | Methylene chloride (0.5) |   |
| Com. Ex. 2 | MMA | (99) | — | CQ DMA | (0.8) (0.4) | Acetone (1) | 50 |

Note 1:
MMA: Methyl methacrylate
1G: Ethyleneglycol dimethacrylate
2G: Diethyleneglycol dimethacrylate
BD: 1,4-Butanediol dimethacrylate
Note 2:
CQ: Camphorquinone
DMA: Dimethylaminoethyl methacrylate
BPT: 4-(4-Butoxyphenyl)-2,6-diphenylthiopyrylium fluoroborate
TBT: Tri(t-butylperoxy)trimellitate

EXAMPLES 6 to 8

Preparation of Organic Filler

Each of the organic fillers having the compositions as set forth in Table 4 was synthesized by an ordinary solution polymerization process while using benzene as the solvent and 2,2'-azobisisobutylonitrile as the polymerization initiator. Each organic filler was precipitated in petroleum ether to obtain a solid copolymer. The weight average molecular weights of respective organic fillers were determined by the GPC method. The results are shown in Table 4.

PREPARATION OF DENTAL PASTE

Each of the light polymerization initiators and the organic fillers, as set forth in Table 5, was dissolved in each mixture of ethylenic unsaturated monomer to prepare a solution. The solution was charged into a kneader and fine particles of an inorganic filler were slowly added thereto, and the admixture was kneaded at atmospheric pressure for 2 hours. The admixture was kneaded under a reduced pressure of lower than 20 mmHg for additional 2 hours to be defoamed, whereby a dental composition paste of the present invention was prepared.

TEST

Each of the pastes having the compositions as set forth in Table 5 was irradiated by a projector including four halogen lamps (150 watts) for a pre-set time period to obtain a cured product. The tackiness of the surface of the molded paste was observed by a finger touch test. The bending strength of each cured product was measured by the method mentioned hereinabove.

TABLE 4

| Organic filler |   | Mixing Ratio (wt %) | Weight Average Molecular Weight |
|---|---|---|---|
| (C)-1 | Methoxyethyl Methacrylate | 5 | 113,000 |
|   | Methoxydiethyleneglycol Monomethacrylate | 60 |   |
|   | Methyl Methacrylate | 35 |   |
| (C)-2 | Methoxytetraethyleneglycol Monomethacrylate | 50 | 152,000 |
|   | Methyl Methacrylate | 45 |   |
|   | Ethyl Acrylate | 5 |   |

TABLE 5

| Example | Ethylenic unsaturated monomer Note 1 | (wt. part) | Organic filler (wt. part) | Inorganic filler Note 2 | (wt. part) | Initiator | (wt. part) | Bending strength (Kg/cm²) | Tackiness |
|---|---|---|---|---|---|---|---|---|---|
| 6 | 3G | (34) | (C)-1 (2) | S-1 | (30) | BTTB | (0.6) | 1110 ± 50 | No |
|   | MDEPP | (34) |   |   |   | MBM | (0.006) |   |   |
| 7 | 3G | (30) | (C)-2 (2) | S-1 | (38) | BTTB | (0.6) | 1010 ± 80 | No |
|   | MDEPP | (30) |   |   |   | MBM | (0.006) |   |   |
| 8 | 3G | (34) | (C)-1 (2) | S-2 | (30) | BTTB | (0.6) | 1220 ± 130 | No |
|   | MDEPP | (34) |   |   |   | MBM | (0.006) |   |   |

Note 1:
3G: Triethyleneglycol Dimethacrylate
MDEPP: 2,2-Bis(4-methacryloxydiethoxyphenyl)propane
Note 2:
S-2: Silica treated with hexamethyldisilazane and having an average particle size of 15 mμ

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A light curable dental liquid or paste comprising an ethylenic unsaturated monomer, a light polymerization initiator and an organic filler, said light polymerization initiator comprising a combination of an organic peroxide and a pyrylium salt compound represented by the following general formula (I) of:

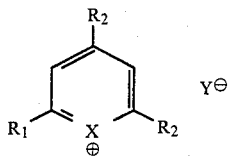

wherein $R_1$, $R_2$ and $R_3$ each represents the same or different atom or group and stands for a hydrogen atom, a halogen atom, an alkyl group, a haloalkyl group, an ethylenyl group, a styryl group, an alkoxy group, a phenyl group, a naphthyl group, an alkylphenyl group, an alkylstyryl group, an alkylnaphthyl group, an alkoxyphenyl group, an alkoxystyryl group, an alkoxynaphthyl group, a hydroxyphenyl group, a hydroxystyryl group, a hydroxynaphthyl group, a halophenyl group, a halostyryl group, a halonaphthyl group, a nitrophenyl group, a nitrostyryl group, a nitronaphthyl group, a aminophenyl group, an aminostyryl group, an aminonaphthyl group, an alkylaminophenyl group, an alkylaminostyryl group, an alkylaminonaphthyl group, a nitro group, an amino group or a hydroxyl group, X stands for an oxygen atom or a sulfur atom and Y for an anionic functional group, said organic peroxide being a tetraperoxy ester containing a benzophenone group and represented by the following general formula (II) of:

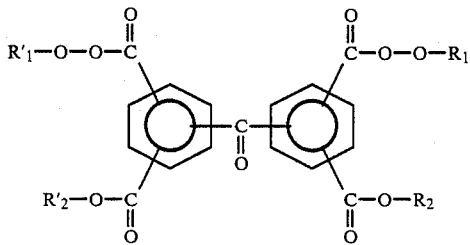

wherein $R_1$ and $R'_1$ each represent a tertiary alkyl group having 4 to 8 carbon atoms and $R_2$ and $R'_2$ each represents a tertiary alkoxy group having 4 to 8 carbon atoms, said organic filler being a polymer obtained by polymerizing a feed monomer containing at least an ester of carboxylic acid selected from the group consisting of acrylic acid, methacrylic acid and mixtures thereof, said feed monomer further containing an unsaturated comonomer copolymerizable with and different from said ester of carboxylic acid, said unsaturated comonomer being represented by the following general formula (III) of:

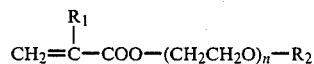

wherein $R_1$ is a hydrogen atom or a methyl group, $R_2$ is an alkyl group having 1 to 4 carbon atoms or a phenyl group, and n is an integer of 1 to 15.

2. A light curable dental liquid or paste as claimed in claim 1, wherein 0.0001 to 1 part by weight of said pyrylium salt compound is added to 100 parts by weight of said ethylenic unsaturated monomer.

3. A light curable dental liquid or paste as claimed to claim 1, wherein 0.001 to 10 parts by weight of said organic peroxide is added to 100 parts by weight of said ethylenic unsaturated monomer.

4. A light curable dental liquid or paste or claimed in claim 1, wherein said ethylenic unsaturated monomer is a derivative of methacrylic acid.

5. A light curable dental liquid or paste as claimed in claim 4, wherein said derivative of methacrylic acid is selected from the group consisting of triethyleneglycol dimethacrylate, hexamethyleneglycol dimethacrylate, 2,2-bis[4-(3-methacryloxy-2-hydroxypropoxy)phenyl]-propane, di-2-methacryloxyethyl-2,2,4-trimethylhexamethylene dicarbamate, 1,2-bis(3-methacryloxy-2-hydroxypropoxy)ethane, tetramethylolmethane trimethacrylate, 2,2-bis(4-methacryloxyethoxyphenyl)-propane, polypropyleneglycol diemthacrylate, methyl methacrylate, 2,2-bis(4-methacryloxypolyethoxyphenyl)propane and mixtures.

6. A light curable dental liquid or paste as claimed in claim 1, wherein said pyrylium salt compound is selected from the group consisting of 4-(4-butoxyphenyl)-2,6-bis(4-methoxyphenyl)pyrylium fluoroborate, 4-(4-butoxyphenyl)-2,6-bis(4-methoxyphenyl)thiopyrylium fluoroborate, 2,6-bis(4-methoxyphenyl)-4-phenylthiopyrylium fluoroborate, 4-(4-butoxyphenyl)-2,6-diphenylpyrylium fluoroantimonate, 4-(4-dimethylaminophenyl)-2,6-diphenylthiopyrylium perchlorate, 2,4,6-tri(4-methoxyphenyl)thiopyrylium fluoroborate and mixtures thereof.

7. A light curable dental liquid or paste as claimed in claim 1, wherein said ester of carboxylic acid is selected from the group consisting of methyl acrylate, methyl methacrylate, ethyl acrylate, ethyl methacrylate, propyl acrylate, propyl methacrylate, butyl acrylate, butyl methacrylate and mixtures thereof.

8. A light curable dental liquid or paste as claimed in claim 1, wherein said polymer is a linear polymer containing not less than 80% by weight of units of said ester of said carboxylic acid and having a weight average molecular weight of not more than 500,000.

9. A light curable dental liquid or paste as claimed in claim 1, wherein said unsaturated comonomer is selected from the group consisting of methoxyethyl acrylate, methoxyethyl methacrylate, phenoxyethyl acrylate, phenoxyethyl methacrylate, methoxydiethyleneglycol acrylate, methoxydiethyleneglycol methacrylate, methoxytetraethyleneglycol acrylate, methoxytetraethyleneglycol methacrylate, isobutoxytetraethyleneglycol acrylate, isobutoxytetraethyleneglycol methacrylate, ethoxypolyethyleneglycol acrylate, ethoxypolyethyleneglycol methacrylate, isopropoxypolyethyleneglycol acrylate, isopropoxypolyethyleneglycol methacrylate, isobutoxypolyethyleneglycol acrylate, isobutoxypolyethyleneglycol methacrylate, methoxypolyethyleneglycol acrylate, methoxypolyethyleneglycol methacrylate, phenoxypolyethyleneglycol acrylate, phenoxypolyethyleneglycol methacrylate and mixtures thereof.

10. A light curable dental liquid or paste according to claim 1, comprising 10 to 99.9 parts by weight of said ethylenic unsaturated monomer and 0.1 to 90 parts by weight of said organic filler.

11. A light curable dental liquid or paste according to claim 1, further comprising an inorganic filler.

12. A light curable dental liquid or paste according to claim 11, wherein said inorganic filler is selected from the group consisting of apatite, soda-lime glass, quartz, silica, borosilicate glass, alumina, barium oxide, zirconium glass and mixtures thereof.

13. A light curable dental liquid or paste according to claim 12, wherein said silica has an average particle size of from 1 to 100 millimicrons and is treated to be hydrophobic with a treating agent selected from the group consisting of dimethyldichlorosilane, hexamethyldisilazane, octyltrimethoxysilane and silicone oils.

14. A light curable dental liquid or paste according to claim 11, comprising 10 to 99.9 parts by weight of said ethylenic unsaturated monomer, 0.1 to 90 parts by weight of said organic filler and 5 to 50 parts by weight of said inorganic filler.

* * * * *

UNITED STATES PATENT AND TRADEMARK OFFICE
CERTIFICATE OF CORRECTION

PATENT NO. : 4,824,876
DATED : April 25, 1989
INVENTOR(S) : Matsumoto et al

It is certified that error appears in the above-identified patent and that said Letters Patent is hereby corrected as shown below:

Please include an asterisk before the date of the patent as follows:

--April 25, 1989--.

Between [73] and [21], please insert the following:

--[*] Notice: The portion of the term of this patent subsequent to May 24, 2005 has been disclaimed.--

Signed and Sealed this

Twenty-seventh Day of February, 1990

*Attest:*

JEFFREY M. SAMUELS

*Attesting Officer*   *Acting Commissioner of Patents and Trademarks*